(12) United States Patent
Koetke

(10) Patent No.: US 6,624,932 B2
(45) Date of Patent: Sep. 23, 2003

(54) ILLUMINATING DEVICE FOR A SURGICAL MICROSCOPE

(75) Inventor: Jochen Koetke, Hamburg (DE)

(73) Assignee: Moller-Wedel GmbH, Wedel (DE)

( * ) Notice: Subject to any disclaimer, the term of this patent is extended or adjusted under 35 U.S.C. 154(b) by 0 days.

(21) Appl. No.: 09/736,534

(22) Filed: Dec. 13, 2000

(65) Prior Publication Data
US 2002/0018292 A1 Feb. 14, 2002

(30) Foreign Application Priority Data
Dec. 15, 1999 (EP) .............................. 99125019

(51) Int. Cl.⁷ .................... G02B 21/06; G02B 21/00
(52) U.S. Cl. .................. 359/389; 359/368; 359/385
(58) Field of Search ............. 359/368–390; 351/200–246

(56) References Cited

U.S. PATENT DOCUMENTS

| 4,674,845 A | * | 6/1987 | Matsumura | 359/385 |
|---|---|---|---|---|
| 4,744,642 A | * | 5/1988 | Yoshinaga et al. | 359/368 |
| 5,126,877 A | * | 6/1992 | Biber | 359/389 |
| 5,155,509 A | * | 10/1992 | Kleinberg | 351/205 |
| 5,555,125 A | * | 9/1996 | Peng | 359/198 |
| 5,627,613 A | * | 5/1997 | Kaneko | 351/221 |
| 5,760,952 A | * | 6/1998 | Koetke | 359/389 |
| 5,898,518 A | * | 4/1999 | Biber | 359/385 |

FOREIGN PATENT DOCUMENTS

JP 9-105866 * 4/1997 .............. 359/389

* cited by examiner

Primary Examiner—Thong Nguyen
(74) Attorney, Agent, or Firm—Alix, Yale & Ristas, LLP

(57) ABSTRACT

The illuminating device for a surgical microscope, with the aid of which the illumination is performed through the microscope objective (4), is defined in that the angles of the incident light (1a, 1b) with the optical axis (11) of the microscope objective (4), and also the intensity of the various light beams can be varied independently of one another with the aid of two reflecting elements (9, 10) which can be displaced independently of one another.

15 Claims, 5 Drawing Sheets

ILLUMINATING DEVICE FOR A SURGICAL MICROSCOPE

BACKGROUND OF THE INVENTION

1. Field of the Invention

The invention relates to an illuminating device for a surgical microscope, having a light source with the aid of which the observed object can be illuminated through a region of the microscope objective situated outside the optical axis, and having two reflecting elements which can be displaced perpendicular to the optical axis, of which the first deflects a portion of the light into a direction perpendicular to the optical axis, and the second deflects this light into an axially close region.

2. Description of the Related Art

Illuminating devices for surgical microscopes mostly use for the illumination a light path which forms only a small angle, frequently in the range of approximately 6°, with the observing beam path. This is important, for example, when it is desired to observe deeper lying regions during an operation. If the illumination is not approximately parallel to the observing beam path, the region to be observed would then lie in shadow.

Ophthalmic surgical operations place special demands on the illumination. The angle at which the eye is illuminated relative to the observing beam path of the surgeon is important. Good plasticity (i.e., visual characteristics, among them contrast and depth of field) of the image by the formation of shadows on structures in the interior of the eye is achieved in the case of illumination of the eye at an angle of a few degrees, frequently at about 6° to the observing beam path. If, by contrast, the eye is illuminated as coaxially as possible relative to the observing beam path (that is to say, the angle between the observing beam path and illuminating beam path is as small as possible), this leads to the formation of the so-called red reflex. The pupil of the operated eye is lit up in a reddish fashion by the light backscattered from the retina. This type of illumination is very advantageous in cataract operations, because tissue remnants which occur upon removal of the lens and are to be removed without fail to prevent complications can be effectively detected in the backlighting of the red reflex. The generation of the red reflex has become an important aid in modern operating techniques.

In addition to the red-reflex illumination, the simultaneous illumination at about 6° is advantageous, because the above mentioned plasticity of the image cannot be achieved at the small angels between the illuminating and observing beam paths required for generating the red reflex. However, a red reflex is not desired in all stages of the operation. An optimum illumination module must therefore offer two illumination settings: in the first position, the OP field is illuminated by a combination of the 6° illumination and the more coaxial illumination for the generation of the red reflex. Only illumination at 6° is performed in the second position.

It is known to deflect a portion of the axially remote light and to use it for axially close illumination (U.S. Pat. No. 4,779,968). The corresponding deflecting devices are, however, attached below the microscope objective, and this reduces the maneuvering distance below the microscope. Also made use of there in the convergent beam path is a beam splitter which runs through the observing beam path, and this impairs the optical quality of the microscope.

It is known to split the light coming from the illumination, a first mirror, which produces the axially remote light, passing a portion of the light onto a second, axially close mirror for axially close illumination (DE 4028 605 A1). This second mirror can be displace perpendicular to the optical axis of the microscope objective such that it is possible to vary the angle formed by the axially close illuminating light with the optical axis of the microscope objective. However, it is not possible for this arrangement to be entirely excluded from the beam path. Because of the deflection with at least two separate deflecting mirrors, this leads to messy imaging of the precision illuminating slit of a microscope slit lamp. Double images are produced.

In a further previously known illuminating device for a surgical microscope (U.S. Pat. No. 5,760,952), the light incident perpendicular to the optical axis o the microscope objective impinges on two deflecting mirrors by means of which the illuminating angle of the axially remote illumination can be varied, and it is possible to influence the quantity of the light which impinges on a further deflecting mirror for the axially close illumination. The angle of the axially close illumination can, however, not be varied.

In an illuminating device of the type mentioned at the beginning (U.S. Pat. No. 4,783,159, FIG. 5), the two reflecting devices can be displaced jointly into the illuminating beam path and out of the same, such that the illumination with the axially close beam can be switched on and off. If the axially close illumination is to be dispensed with, the reflecting elements must be removed from the beam path. The illumination with the axially close beam is performed, however, always on the optical axis of the objective lens; the illuminating angle cannot be varied.

SUMMARY OF THE INVENTION

The object of the invention consists in creating an illuminating device of the type mentioned at the beginning which has a greater variability and with the aid of which the angle of the axially closed illumination can be varied.

In the case of an illuminating device of the type mentioned at the beginning, the solution according to the invention consists in that the reflecting elements can be displaced independently of one another.

By displacing the first reflecting element, it is possible to vary the light quantity which impinges on the second reflecting element. A more or less strong red reflex can be produced thereby. If the first reflecting element is pushed completely out of the beam path of the axially remote illumination, absolutely no axially close light is directed to the object for the red reflex. If the first reflecting element is slowly pushed from outside into the beam path of the axially remote illumination, the red reflex is amplified. At the same time, the axially remote regions of the axially remote illumination are covered, such that the angle between the axially remote light still being shone in and the optical axis of the microscope objective is also reduced. If the red reflex is in the meantime to be dispensed with, the first reflecting element is pushed out of the beam path. If the red reflex is subsequently to be produced again, this is achieved after reintroducing the first reflecting element into the beam path at the same angle for the axially close illumination, since the position of the second reflecting element has not been varied for excluding the red reflex.

Since the second reflecting element can be displaced, the angle for the axially close illumination with respect to the observing beam path can be decreased, and thus the quality of the red reflex can be improved as a function of the setting of the magnification factor of the microscope by zoom or Galilei changer. In the case of higher magnification factors, this reflecting element can be placed by the user close to the observing beam paths or even overlapping therewith (thus producing a more intensive red reflex), without unwanted vignetting becoming detectable. Vignetting can occur if the reflecting element is set in a fashion overlapping with the observing beam path in the case of relatively small magnification. Instances of darkening which are felt as disturbing by many users can occur occasionally in the microscope image perceived by the user. Of course, with acceptance of vignetting it is also possible in the case of low magnifications to displace the second reflecting element so far into the beam paths for an improved red reflex that vignetting becomes visible. The user can make the best choice for the concrete situation.

BRIEF DESCRIPTION OF THE DRAWINGS

The invention is described below with the aid of an advantageous embodiment with reference to the attached drawings, in which.

DETAILED DESCRIPTION OF THE PREFERRED EMBODIMENT

Figures 1, 2:
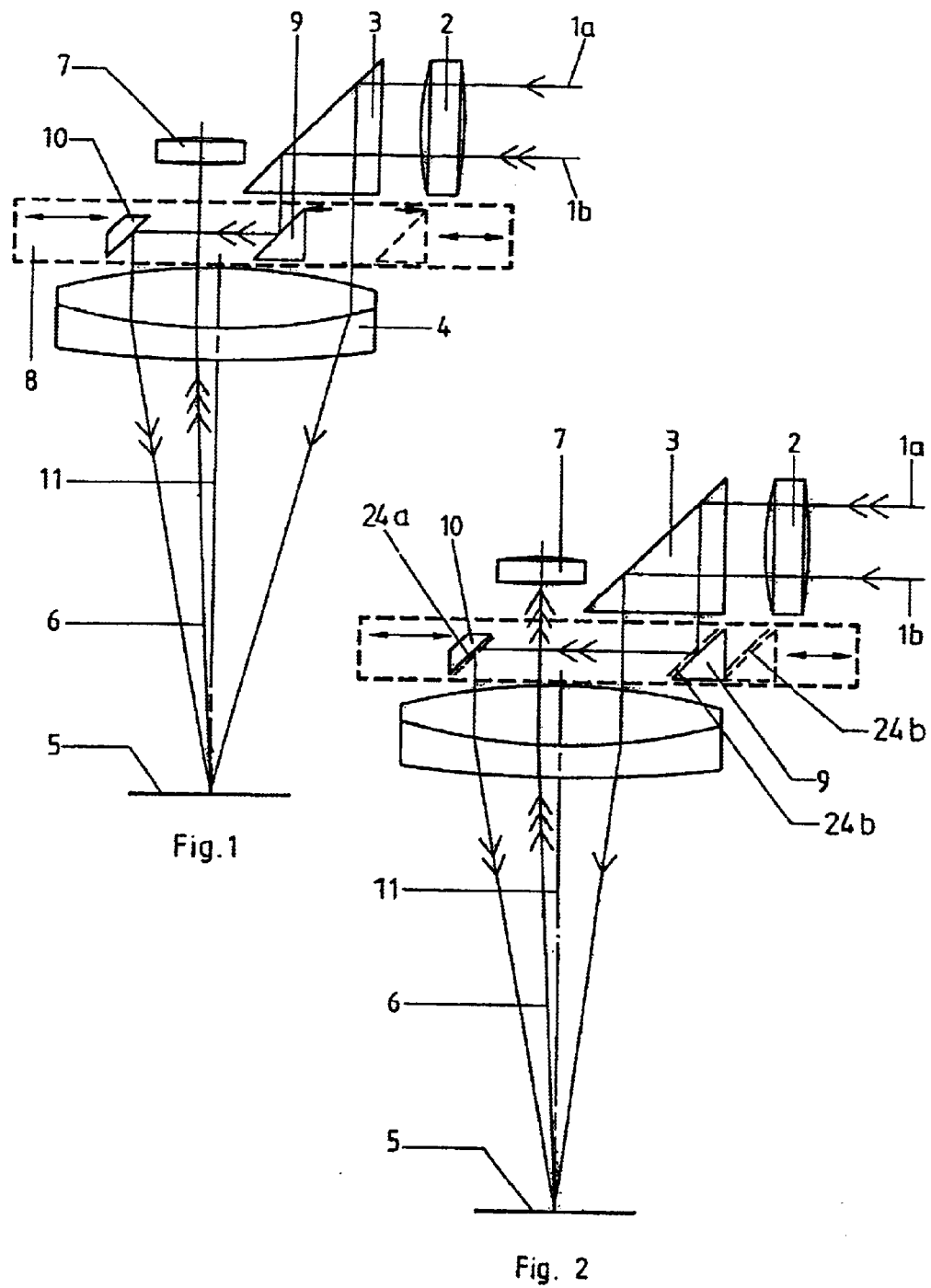
FIGS. 1 and 2 show a schematic illustration of the mode of operation of the illuminating device according to the invention for different positions of the reflecting elements.

As is shown in FIGS. 1 and 2, light beams 1a and 1b, marked by one or two arrows, respectively, pass from a light source (not shown) through a lens 2 to a deflecting prism 3 which directs the axially remote beam 1 a onto the observation object 5 through the objective lens 4. The observation is then performed on the path of the beam 6 through a lens 7 and further optical elements, which are customary in a microscope and are not shown in these illustrations. Located immediately behind the objective 4 is a module, indicated at 8 by dashes, with two reflecting elements in the form of mirrors. Both the first reflecting element 9, arranged on the right, and the second reflecting element 10, arranged on the left, can be displaced, as is shown by arrows. If the first mirror 9 is located in the dashed position in FIG. 1, the entire light 1a, 1b is directed in a fashion remote from the axis onto the object 5. If the mirror 9 is located in the position illustrated with full lines in FIG. 1, a portion of the light, specifically 1b, is directed onto the second mirror 10, and directed from there onto the object 5 at a smaller angle relative to the optical axis 11 of the microscope objective 4.

The difference in the positions of the mirrors 9, 10 in FIG. 2 relative to FIG. 1 consists in that the mirror 9 directs axially remote light 1a onto the second mirror 10, and axially close light 1b additionally serves the purpose of illumination. This is the case of overall small angles of illumination, which increases the red reflex.

By contrast with previously known illuminating devices, the first reflecting element 9 may be moved out of the illuminating beam path while not in use. It is only by complete removal that the highest imaging quality can be ensured for the use of a surgical slit lamp which projects a fine optical slit into the observing plane. In the case of the previously known illuminating device (U.S. Pat. No. 5,760,952), with the red reflex amplifier switched off the projection of a fine light slit of the slit lamp requires very precise adjustment of two mirrors relative to one another, of which one is movable. In practice, this cannot be fulfilled with a reasonable outlay, and so quality impairments must be accepted with reference to imaging. The adjustment is clearly less critical for the illuminating device according to the invention, because the red reflex amplification necessitates substantially fewer requirements of the imaging accuracy, and the first reflecting element 9 can be moved completely out of the illuminating beam path for slit lamp applications.

Thus, the illuminating angle can be varied for all the light 1a, 1b or else only for a portion of the light 1b. There is a need for this possibility in ophthalmology and in general whenever the illuminating angle is to be adapted to the respective operating situation. In many cases, there is a need in ophthalmology to produce the red reflex or fundus reflex for reliable operation. In other situations, it can be favorable to enlarge the illuminating angle, in order to increase the plasticity of the image perceived by casting stronger shadows on the observed structures. All this is possible with the aid of the illuminating device according to the invention.

By varying the position of the first reflecting element 9, it is possible, for example, to select the component with the small angle to the observing beam path or with the large angle to the observing beam path. In ophthalmology, the first reflecting element 9 can be positioned such that the reflection of the axially remote illumination on the patient's cornea appears to the operating surgeon as a reflection. In other disciplines, it is advantageous to position the first reflecting element in the middle of the axially remote illumination, because then the light quantity directed onto the second reflecting element is a maximum.

By contrast with previously known illuminating devices, in the case of the illuminating device according to the invention the optical axis of the red reflex illumination deliberately does not coincide with the optical axis of the microscope objective 11 and the observing beam paths 6. Absolute coincidence leads, specifically, to a "flat image" of unsatisfactory plasticity. Moreover, the mirror width is limited to small values in the case of absolute coincidence, because otherwise the observing beam paths are covered. The light quantity is therefore insufficient for most operation stages, such as "polishing" of the rear lens capsule, known as phako-emulsification.

In an advantageous embodiment, the two reflecting elements 9, 10 and the displacing mechanism are arranged in a removable module 8. The module 8 is installed between the microscope objective 4 and the microscope's integrated axially remote illumination, which directs the light of the illuminating source to the microscope objective 4. Accessories of the microscope, for example, assistants' microscopes, can be installed in front of and behind the module 8. The module 8 can be installed directly behind the microscope objective 4, or else in any desired sequence with other modular accessories, for example directly in front of the axially remote illumination. Positioning directly behind the microscope objective in order to keep low the scattering of reflections of the illumination into the observing beam path is advantageous. Retrofitting at the customer's is also possible without difficulty.

In an advantageous embodiment, the first reflecting element 9 is provided with a stop 17 on its side pointing away from the optical axis 11. It is thereby possible to cover an axially remote light 1a if the reflecting element is displaced closer to the optical axis 11 of the microscope objective 4. However, it can also be provided that the stop is partially transparent to light so that a weaker component of the axially remote light 1a can still reach the object to be illuminated.

To control the amount of light deflected from the first reflecting element 9 onto the object, the first reflecting element 9 can be provided with a stop 25 placed on the side of the first reflecting element facing the objective 4. Here and in other portions of this application the term "stop" refers to a light stop which partly or totally blocks the light. The size and position of this stop 25 can be chosen in a way that light from the prizm 3 is blocked completely when this reflecting element is placed in the center of the illumination for high intensity and good contrast of the red reflex, but lower overall illumination intensity in the object plane. When the first reflecting element 9 is withdrawn from the illumination path, the stop 25 allows part of the light pass to the object.

It is possible to take measures such that the first and/or second reflecting element relays shortwave components (i.e., shortwave visible or blue light) of the reflected light only in an attenuated fashion, by, for example, being provided with a filter or an appropriate coating 24a, 24b. If the reflecting element is a prism, this could be produced from a material which attenuates the shortwave component during passage of the light. Apart from prisms or in addition to prisms, it is also possible to use mirrors as reflecting elements.

The reflecting elements 9, 10 can advantageously be displaced with the aid of coaxial rotating knobs.

Figure 4:
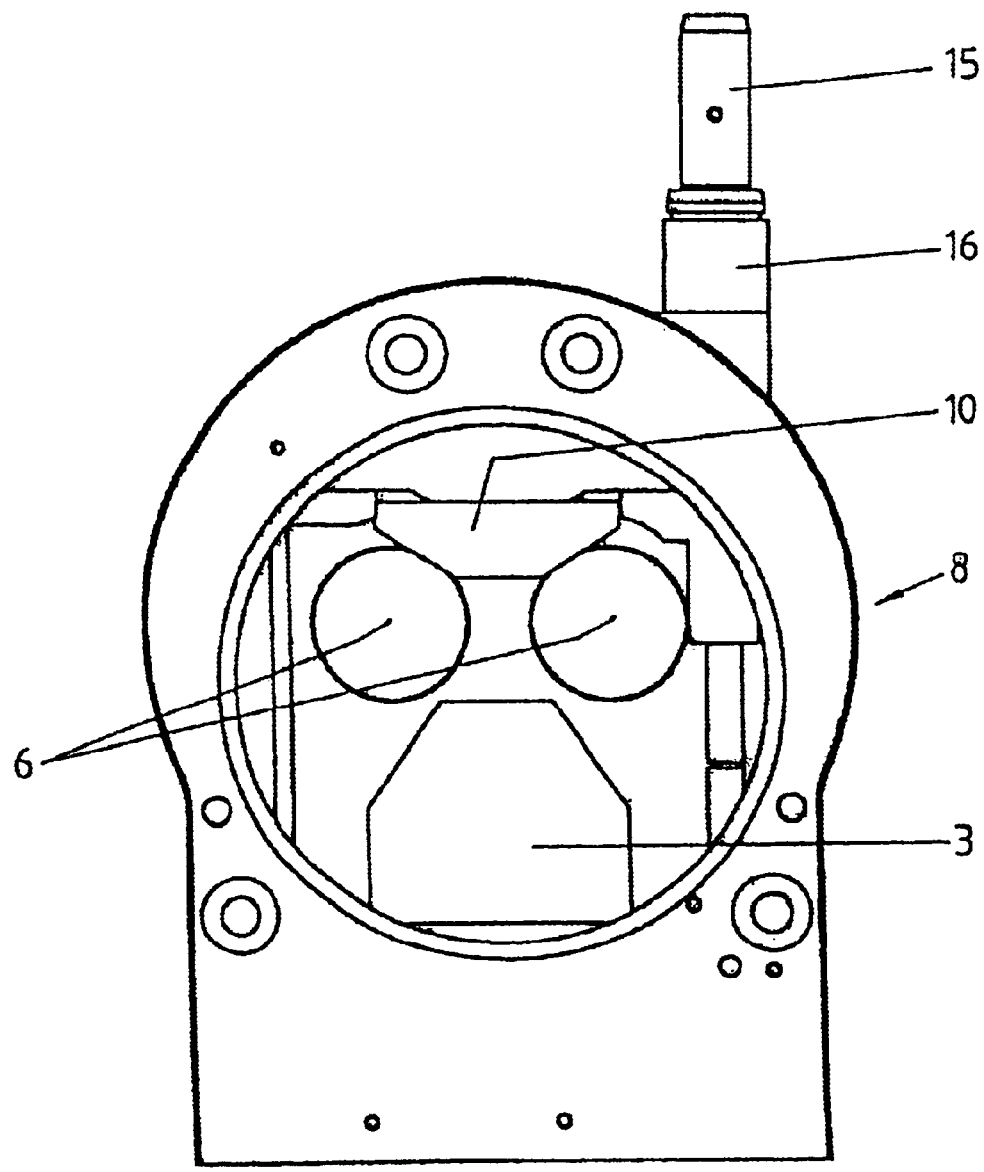
FIG. 4 shows a view of the essential parts from below.
Figure 5:
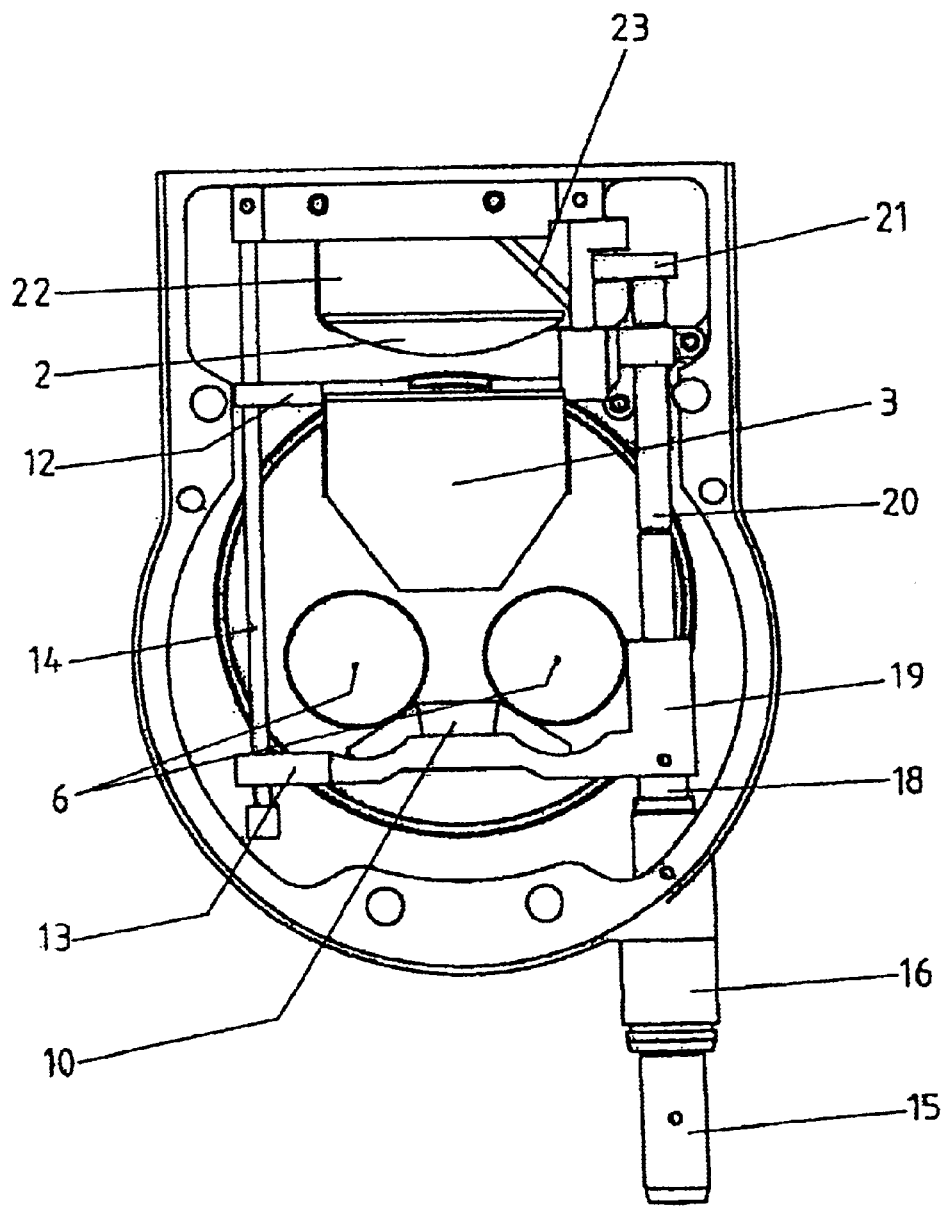
FIG. 5 shows a corresponding view of the essential parts of the illuminating device from above.

As best illustrated in FIGS. 4 and 5, it is expedient for the boundary, directed toward the observing beam paths 6, of the second reflecting element 10 to be parallel to the tangent of the circumference of those beam paths at which the reflecting elements approach this beam path. This boundary can, however, also be configured such that it then embraces the beam paths in the shape of parts of a circle.

Figure 3:
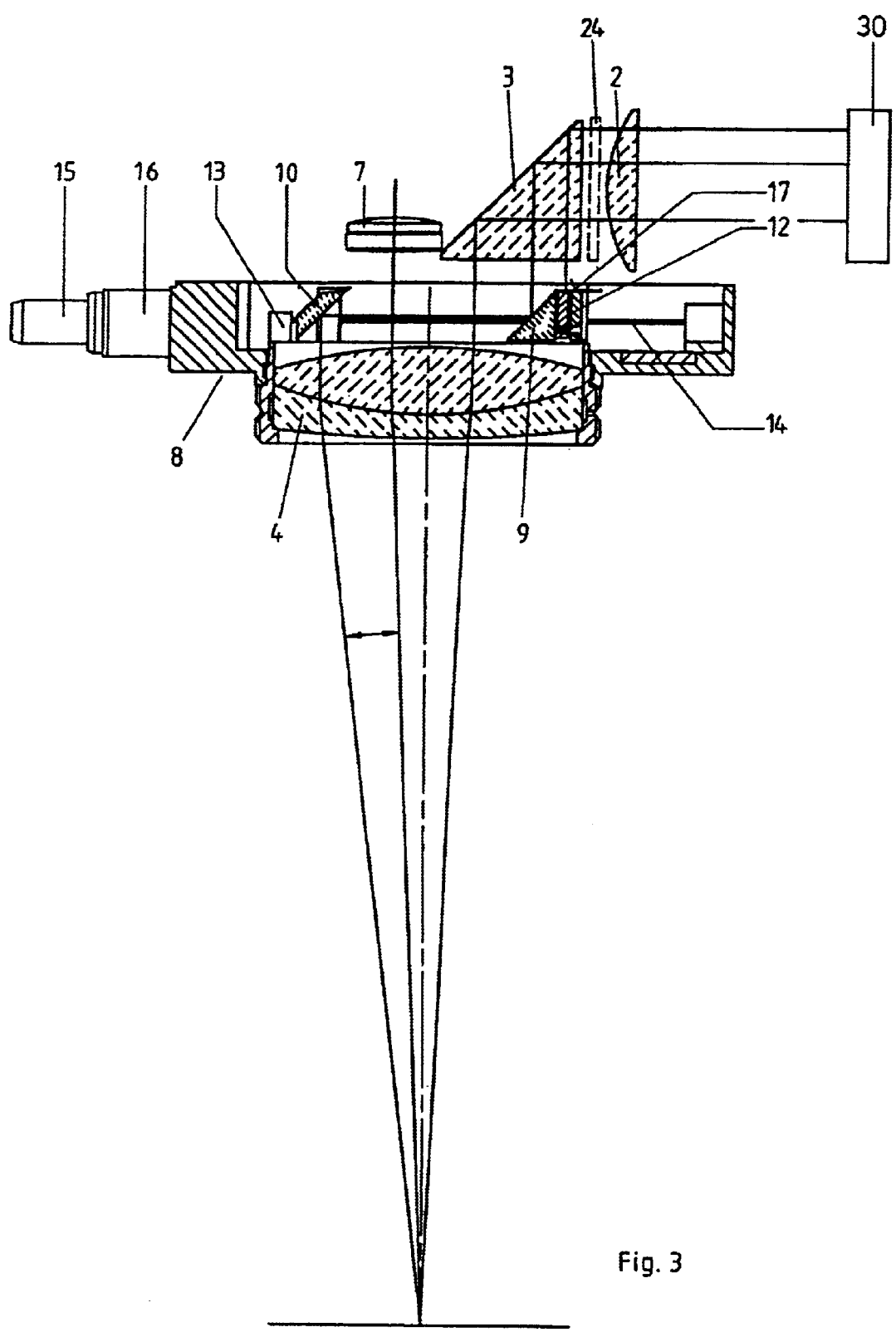
FIG. 3 shows a section through the essential part of the illuminating device, seen from the side.

The housing 8, which is of modular design here, is shown in greater detail in FIG. 3 together with the two displaceable mirrors 9, 10. These mirrors are mounted on slides 12, 13 which can slide on rails 14. The two mirrors 9, 10 are adjusted in this case independently of one another by the coaxial rotating knobs 15, 16. A stop 17 for blocking light is arranged behind the mirror 9. Indicated at 24 by dashes is a filter with the aid of which the shortwave component of the light is attenuated.

FIG. 4 shows the essential parts of the illuminating device according to the invention from below. It is to be seen there that the second mirror 10 just touches the two observing beam paths 6 of the stereomicroscope. Its boundary surface is tangential in this case to the circumference of the observing beam paths 6, but could also be provided with cutouts in the shape of parts of a circle and partially embrace the beam paths 6 (not shown). As mentioned, in order to vary the angle for the red reflex, this mirror can, however, also be moved closer to the observing beam paths or further away from the same.

FIG. 5 shows the module 8 from above. The rotating knob 16 is connected to a threaded rod 18 which goes through a nut 19 which is arranged on the slide 13. When the rotating knob 16 is rotated, this causes the slide 13 to move with the second mirror 10 in one or other direction. Guided coaxially through the element 16 is a spindle 20 which is connected to the rotating knob 15. Located at the end of this spindle 20 is a cam 21 by means of which a plate 22 can be moved to the right or left. This plate has a groove 23 into which a pin of the slide 12 fits. If the plate 22 is moved to the right and left in the figure by rotating the knob 15, the slide 12 moves with the mirror 9 arranged thereupon (covered in FIG. 5 by the prism 3) in one or other direction. The mirror 9 can be adjusted very considerably and quickly with this cam control by a relatively slight rotation of the rotating knob 15.

Figure 6:
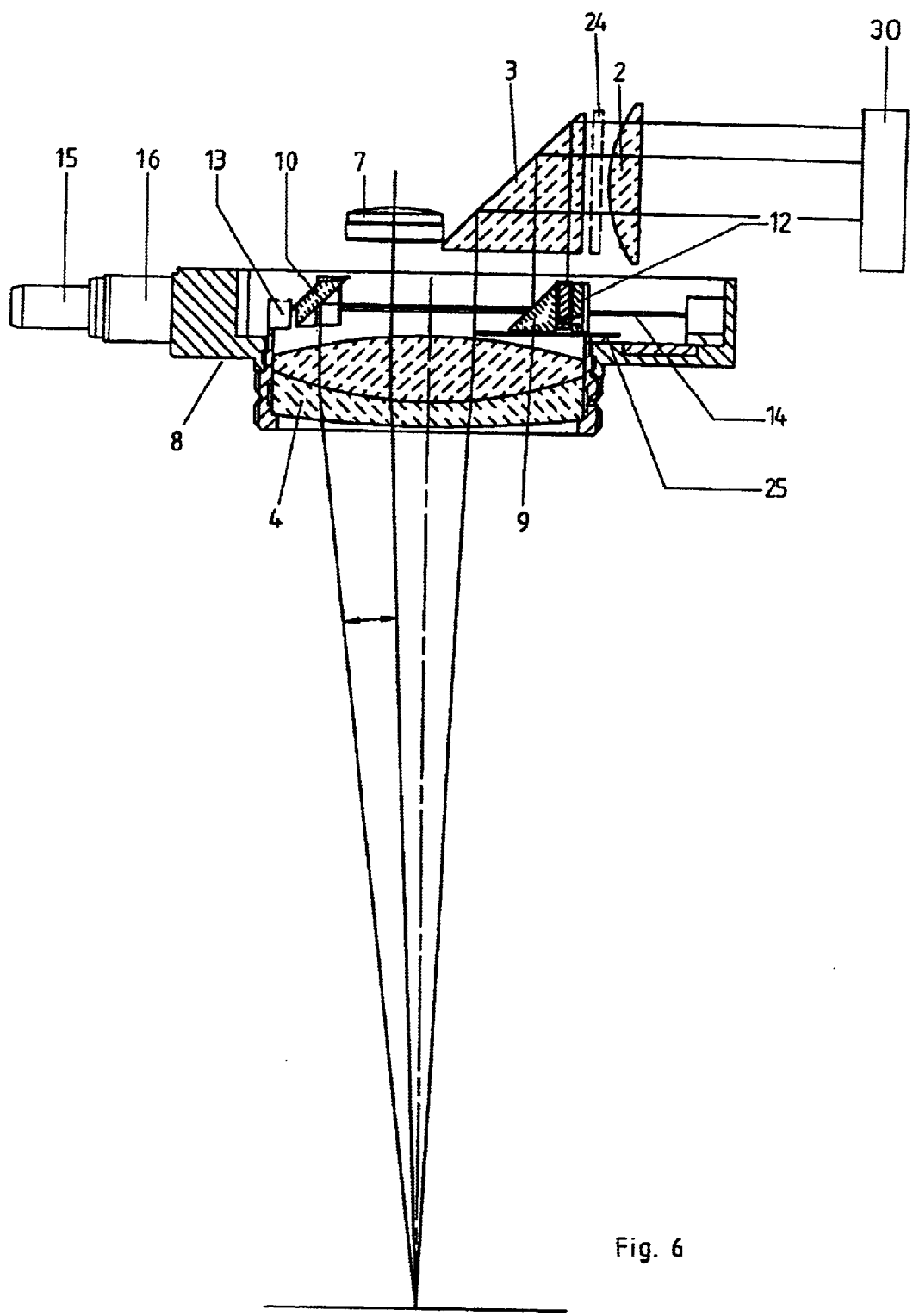
FIG. 6 shows in a similar view as in FIG. 3 a further embodiment.

FIG. 6 shows a further embodiment of the invention. To control the amount of light deflected from prism 3 onto the object 5, the mirror 9 can be provided with a light stop 25, placed on the side of the mirror 9 facing the objective 4. The size and position of stop 25 can be chosen in such way that light from prism 3 is blocked completely when mirror 9 is placed in the center of the illumination from prism 3 for high intensity and good contrast of the red reflex, but lower overall illumination intensity in the plane of object 5. When mirror 9 is withdrawn from the illumination path, stop 25 lets part of the light deflected from prism 3 pass to object 5.

What is claimed is:

1. A surgical microscope comprising:
    an objective lens having an optical axis, a front side facing an object to be observed and an axially opposed rear side;
    an illumination light deflector axially spaced from and behind said objective lens, said illumination light deflector deflecting illumination light into a region of said objective lens radially spaced from said objective lens optical axis and in a direction parallel to said objective lens optical axis;
    a first reflecting element axially intermediate said objective lens and said deflector and moveable perpendicular to said objective lens optical axis to divert a selected portion of said illumination light incident on said objective lens into a direction perpendicular to said objective lens optical axis; and
    a second reflecting element radially opposed to said first reflecting element to redirect the selected portion of illumination light into said objective lens, said second reflecting element moveable perpendicular to said objective lens optical axis to determine a selected radial distance from said objective lens optical axis at which said portion of illumination light enters said objective lens,
    wherein a quantity of illumination light included in said selected portion is dependent upon a position of said first reflecting element relative to said objective lens optical axis.

2. The surgical microscope of claim 1, wherein said first and second reflecting elements are moveable independently of one another.

3. The surgical microscope of claim 2, wherein said first or second reflecting elements attenuate a shortwave component of said illumination light.

4. The surgical microscope of claim 3, wherein said first or second reflecting elements attenuate the shortwave component by means of a filter or a coating.

5. The surgical microscope of claim 1, wherein the first reflecting element is moveable to a position beyond a radial periphery of the objective lens, whereby no illumination light is diverted.

6. The surgical microscope of claim 1, wherein a quantity of light diverted by said first reflecting element is variable by moving said first reflecting element relative to said objective lens optical axis.

7. The surgical microscope of claim 1, wherein said first reflecting element includes a stop extending radially outwardly from a radial outward side of said first reflecting element.

8. The surgical microscope of claim 7, wherein said stop is opaque.

9. The surgical microscope of claim 7, wherein said stop is partially transparent to light.

10. The surgical microscope of claim 1, wherein said first and second reflecting elements attenuate a shortwave component of said illumination light.

11. The surgical microscope of claim 10, wherein said first and second reflecting elements attenuate the shortwave component by means of a filter or a coating.

12. The surgical microscope of claim 1, comprising coaxial rotating knobs and rotation of respective of said knobs causes movement of respective of said first or second reflecting elements.

13. The surgical microscope of claim 1, wherein said first and second reflecting elements comprise a reflector selected from a mirror or a prism.

14. The surgical microscope of claim 1, wherein said first reflecting element has a side facing the objective lens including a stop.

15. The surgical microscope of claim 1, comprising a pair of observation beam paths through said objective lens radially intermediate said first and second reflecting elements and said second reflecting element has a radially inward boundary tangential to said observation beam paths.

* * * * *